US012562276B2

(12) United States Patent
Suk et al.

(10) Patent No.: US 12,562,276 B2
(45) Date of Patent: Feb. 24, 2026

(54) BRAIN IMAGE-BASED QUANTITATIVE BRAIN DISEASE PREDICTION METHOD AND APPARATUS

(71) Applicant: KOREA UNIVERSITY RESEARCH AND BUSINESS FOUNDATION, Seoul (KR)

(72) Inventors: Heung-Il Suk, Seoul (KR); Kwanseok Oh, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 300 days.

(21) Appl. No.: 18/212,261

(22) Filed: Jun. 21, 2023

(65) Prior Publication Data

US 2024/0079139 A1     Mar. 7, 2024

(51) Int. Cl.
*G16H 50/20*     (2018.01)
*A61B 5/00*     (2006.01)
(Continued)

(52) U.S. Cl.
CPC ........... *G16H 50/20* (2018.01); *A61B 5/0042* (2013.01); *A61B 5/4088* (2013.01); *G06T 5/70* (2024.01);
(Continued)

(58) Field of Classification Search
CPC ........ G16H 30/20; G16H 30/40; G16H 50/20; G16H 50/30; G16H 50/50; G06T 5/70;
(Continued)

(56) References Cited

U.S. PATENT DOCUMENTS

2021/0228079 A1*  7/2021  Betrouni ................ G16H 50/30
2023/0162350 A1*  5/2023  Suk ...................... A61B 5/7275

FOREIGN PATENT DOCUMENTS

JP          5699936 B2    4/2015
JP      2020-150989 A    9/2020
(Continued)

OTHER PUBLICATIONS

Oh et al., "Learn-Explain-Reinforce: Counterfactual Reasoning and Its Guidance to Reinforce an Alzheimer's Disease Diagnosis Model", arXiv:2108.09451v1 [cs.CV] Aug. 21, 2021, pp. 1-14. (Year: 2021).*
(Continued)

*Primary Examiner* — Jennifer Mehmood
*Assistant Examiner* — Jose M Torres
(74) *Attorney, Agent, or Firm* — NSIP Law

(57)     ABSTRACT

Disclosed are a brain image-based quantitative brain disease prediction method and apparatus. According to the present invention, there is provided a brain image-based quantitative brain disease prediction apparatus including a processor, and a memory connected to the processor, in which the memory stores program instructions executed by the processor to convert original images of multiple brain images into original radiomic, convert a synthetic image synthesized through counterfactual reasoning of the original image into a synthetic radiomic, estimate a difference between the original radiomic and the synthetic radiomic to extract a representative region of interest for brain disease prediction, and input the representative region of interest and brain images for each patient to a linear classifier including a counterfactual-guided attentive feature representation module to predict a disease state.

10 Claims, 7 Drawing Sheets

(51) Int. Cl.

| | |
|---|---|
| *G06T 5/70* | (2024.01) |
| *G06T 7/00* | (2017.01) |
| *G06T 7/11* | (2017.01) |
| *G06T 7/143* | (2017.01) |
| *G06T 7/168* | (2017.01) |
| *G16H 30/20* | (2018.01) |
| *G16H 30/40* | (2018.01) |
| *G16H 50/30* | (2018.01) |

(52) U.S. Cl.

CPC .......... *G06T 7/0012* (2013.01); *G06T 7/0014* (2013.01); *G06T 7/11* (2017.01); *G06T 7/143* (2017.01); *G06T 7/168* (2017.01); *G16H 30/20* (2018.01); *G16H 30/40* (2018.01); *G16H 50/30* (2018.01); *G06T 2207/10088* (2013.01); *G06T 2207/20076* (2013.01); *G06T 2207/20081* (2013.01); *G06T 2207/20084* (2013.01); *G06T 2207/20224* (2013.01); *G06T 2207/30016* (2013.01)

(58) Field of Classification Search

CPC ....... G06T 7/0012; G06T 7/0014; G06T 7/11; G06T 7/143; G06T 7/168; G06T 2207/10088; G06T 2207/20224; G06T 2207/20076; G06T 2207/20081; G06T 2207/20084; G06T 2207/30016; A61B 5/0042; A61B 5/055; A61B 5/4088; A61B 5/7275

See application file for complete search history.

(56) References Cited

FOREIGN PATENT DOCUMENTS

| | | |
|---|---|---|
| KR | 10-2019-0105452 A | 9/2019 |
| KR | 10-2022-0046058 A | 4/2022 |

OTHER PUBLICATIONS

Oh, Kwanseok, et al, "Born Identity Network: Multi-way Counterfactual Map Generation to Explain a Classifier's Decision." arXiv preprint arXiv:2011.10381 (2020)., (17 pages).

* cited by examiner

ORIGINAL IMAGE AND SYNTHETIC IMAGE

INVERSE-Gaussian NORMALIZATION — S300

INVERSE-QUANTILE NORMALIZATION — S302

UPSCALING — S304

ACQUIRE VOLUME PROBABILITY MAP THROUGH BRAIN REGION SEGMENTATION — S306

ISOTROPIC Gaussian SMOOTHING — S308

JACOBIAN NONLINEAR MODULATION — S310

MAP GRAY MATTER TEMPLATE — S312

ACQUIRE GRAY MATTER DENSITY MAP

BRAIN IMAGE-BASED QUANTITATIVE BRAIN DISEASE PREDICTION METHOD AND APPARATUS

CROSS-REFERENCE TO RELATED APPLICATION

This application claims the benefit under 35 USC 119(a) of Korean Patent Application No. 10-2022-0127951 filed on Oct. 6, 2022, in the Korean Intellectual Property Office, the disclosure of which is incorporated herein by reference in its entirety.

BACKGROUND

(a) Technical Field

The present invention relates to a brain image-based quantitative brain disease prediction method and apparatus, and more particularly, to a method and apparatus capable of quantifying and predicting Alzheimer's disease based on a brain image.

(b) Background Art

Counterfactual reasoning is one of the methods that have recently become a hot topic in the field of eXplainable artificial intelligence.

The counterfactual reasoning is a high-level thought reasoning method of providing, by an artificial intelligence itself, appropriate grounds for decision-making in a form that can be understood by humans and analyzing a causal relationship when artificial intelligence draws wrong conclusion or a reasoning process of the artificial intelligence is wrong by considering a hypothetical alternative event that did not happen.

However, as with various existing XAI methods, the counterfactual reasoning simply provides visual explanations to support decision-making of artificial intelligence, and thus, has interpretative limitations for clinicians to use as auxiliary data for accurate biomarker detection, disease diagnosis, and progression prediction in the medical field.

In this regard, unlike visual explanations that reflect subjective opinions, quantitative feature analysis methods through objective and numerical phenotypic features, such as density, volume, texture, and morphology, have been proposed in conventional oncology.

Based on the advantages of this quantitative feature analysis method, methods of using quantitative values for disease progression according to structural changes in a brain have been proposed in relation to various medical fields, especially brain disease diagnosis and prediction.

At the same time, by combining the existing statistical analysis method and a machine learning method, disease state prediction service for each patient was effectively provided.

However, since the quantitative feature analysis method combined with the existing machine learning method performs analysis and disease prediction only for well-known biomarkers, the quantitative feature analysis method may be accompanied by a problem of manually extracting different numbers of biomarkers or biomarkers for different regions of interest according to the purpose of ongoing research. Therefore, there are limitations in that the quantitative feature analysis method is difficult to generalize. In addition, such an analysis environment may inevitably cause a problem of failing to consider areas that may be considered as potential biomarkers.

SUMMARY OF THE INVENTION

The present invention is to provide a brain image-based quantitative brain disease prediction method and apparatus capable of providing precise numerical interpretation and explanation in clinical aspects.

According to an embodiment of the present invention, a brain image-based quantitative brain disease prediction apparatus includes: a processor; and a memory connected to the processor, wherein the memory stores program instructions executed by the processor to convert original images of multiple brain images into original radiomic, convert synthetic image synthesized through counterfactual reasoning of the original image into a synthetic radiomic, estimate a difference between the original radiomic and the synthetic radiomic to extract a representative region of interest for brain disease prediction, and input the representative region of interest and brain images for each patient to a linear classifier including a counterfactual-guided attentive feature representation module to predict a disease state.

The program instructions may synthesize a normal original image into a brain disease synthetic image and synthesize a brain disease original image into a normal synthetic image using a counterfactual map, before converting into the original radiomic and the synthetic radiomic.

The program instructions may perform preprocessing, brain region segmentation, and denoising to convert the original image and the synthetic image into the original radiomic and the synthetic radiomic.

The preprocessing may include inverse-Gaussian normalization, inverse-quantile normalization, and upscaling for inverse transformation to an image scale of a state before being used as an input of a deep learning model.

A brain region classified by the brain region segmentation includes gray matter, white matter, and cerebrospinal fluid, and a volume probability map may be obtained by the brain region segmentation.

The program instructions may map the volume probability map to a gray matter template to perform structural distortion, apply Jacobian non-linear modulation to a result image from the mapping, and remove noise through isotropic Gaussian smoothing and alleviate a contrast generated in the preprocessing.

The program instructions may calculate the difference between the original radiomic and the synthetic radiomic, estimate a brain disease-related region through an average of absolute values of differences between all the original radiomics and synthetic radiomics, apply a constraint through a statistical percentile threshold to the brain disease-related region to acquire a brain disease-effect map including a brain disease representative region, extract a representative region of interest from a value corresponding to the brain disease representative region in the brain disease-effect map through brain region segmentation, and acquire voxel coordinates corresponding to the representative region of interest.

The program instructions may embed the representative region of interest and the brain images for each patient, respectively, and convert the representative region of interest and the brain images into an embedding matrix, multiply the embedding matrix corresponding to the representative region of interest and the embedding matrix of the brain images for each patient element by element to generate a counterfactual-guided attention map, and predict the disease state using the counterfactual-based attention map and a calculation result of the embedding matrix of the brain images for each patient.

The program instructions may multiply the counterfactual-based attention map and the embedding matrix of the brain images for each patient element by element, and predict the disease state using a result of the multiplication and a result of summing the embedding matrix corresponding to the representative region of interest element by element.

According to another embodiment of the present invention, a brain image-based quantitative brain disease prediction method including a processor and a memory, includes transforming original images of multiple brain images into original radiomic, transforming a synthetic image synthesized through counterfactual reasoning of the original image into a synthetic radiomic, estimating a difference between the original radiomic and the synthetic radiomic to extract a representative region of interest for brain disease prediction, and inputting the representative region of interest and brain images for each patient to a linear classifier including a counterfactual-guided attentive feature representation module to predict a disease state.

According to the present invention, in order to describe deep learning decision-making, by converting the deep learning decision-making into radiomic that may consider quantitative volumetric features, not just performing visual inspection through visual explanations derived from counterfactual reasoning, it is possible to quantitatively demonstrate clinical efficacy and numerically interpret clinical efficacy from the perspective of a radiologist or clinician.

In addition, according to the present invention, by proposing a counterfactual-guided attentive feature representation module that highlights regions of interest that contribute to accurate disease prediction along with representative regions of interest that are considered as landmarks related to Alzheimer's disease progression, it is possible to predictive performance comparable to that of a deep learning model.

Furthermore, according to the present invention, by providing intuitive interpretation of model's decision-making, it is possible to detect potential biomarkers that clinicians are difficult to distinguish during representative biomarker analysis and visual inspection related to the progression of Alzheimer's disease for each patient or each patient group corresponding to each disease stage.

Additionally, by using radiomic for counterfactual reasoning, it is possible to alleviate unbalanced problem of the number of data of disease groups for each age group and the lack of data for specific disease groups that may often occur in real medical environments.

DETAILED DESCRIPTION

Figure 1:
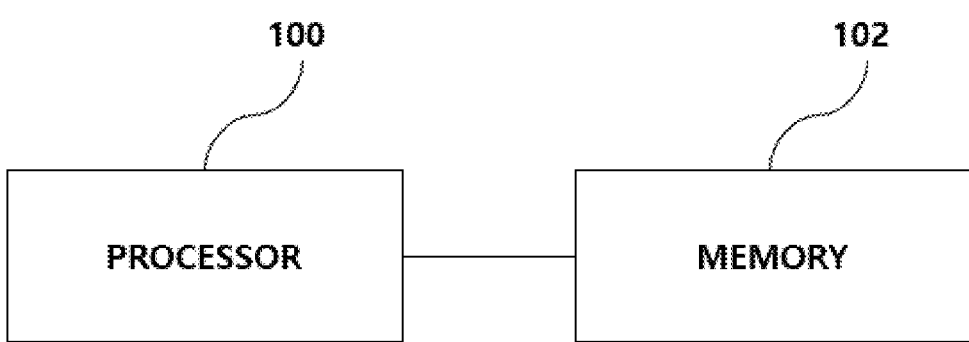
FIG. 1 is a diagram illustrating a configuration of a brain disease prediction apparatus according to a preferred embodiment of the present invention.

Since the present invention may be variously modified and have several exemplary embodiments, specific exemplary embodiments will be illustrated in the accompanying drawings and be described in detail in a detailed description. However, it is to be understood that the present invention is not limited to a specific exemplary embodiment, but includes all modifications, equivalents, and substitutions without departing from the scope and spirit of the present invention.

Terms used in the present specification are used only in order to describe specific exemplary embodiments rather than limiting the present invention. Singular forms are intended to include plural forms unless the context clearly indicates otherwise. It should be further understood that terms "include" or "have" used in the present specification specify the presence of features, numerals, steps, operations, components, parts mentioned in the present specification, or combinations thereof, but do not preclude the presence or addition of one or more other features, numerals, steps, operations, components, parts, or combinations thereof.

In addition, components of the embodiments described with reference to each drawing are not limitedly applied only to the corresponding embodiment, and may be implemented to be included in other embodiments within the scope of maintaining the technical spirit of the present invention. In addition, it goes without saying that these components may also be re-implemented as one embodiment in which a plurality of embodiments are integrated, even if a separate description is omitted.

In addition, in the description with reference to the accompanying drawings, regardless of reference numerals, the same components will be given the same or related reference numerals and duplicate description thereof will be omitted. When it is decided that the detailed description of the known art related to the present invention may unnecessary obscure the gist of the present invention, a detailed description therefor will be omitted.

The present invention relates to a method of enabling quantitative feature analysis on a counterfactually synthetic image through a counterfactual map for decision-making reasons of an Alzheimer's dementia prediction model generated from a counterfactual reasoning method in the field of eXplainable artificial intelligence (XAI) and deriving disease predictive performance comparable to a deep learning model.

FIG. 1 is a diagram illustrating a configuration of a brain disease prediction apparatus according to a preferred embodiment of the present invention.

As illustrated in FIG. 1, the apparatus according to the present embodiment may include a processor 100 and a memory 102.

The processor 100 may include a central processing unit (CPU) capable of executing a computer program, other virtual machines, or the like.

The memory 102 may include a non-volatile storage device such as a non-removable hard drive or a removable storage device. The removable storage device may include a compact flash unit, a USB memory stick, and the like. The memory 102 may also include a volatile memory, such as various random access memories.

The memory 102 according to the present embodiment stores program instructions for predicting brain disease using counterfactual reasoning and a counterfactual-guided attentive feature representation module.

Hereinafter, a process of executing program commands according to the present embodiment will be described in detail, and the following module may be defined as a set of a series of program instructions.

In addition, brain disease will be explained centering on Alzheimer's disease, but is not necessarily limited thereto.

Figure 2:
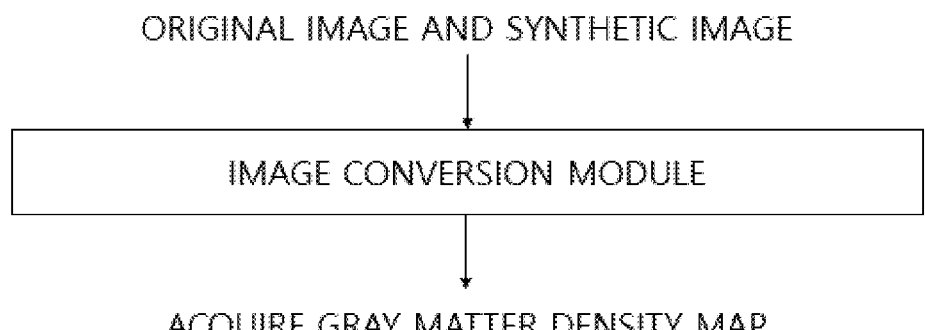
FIG. 2 is a diagram illustrating a process of radiomic acquisition according to the present embodiment.

FIG. 2 is a diagram illustrating a process of radiomic acquisition according to the present embodiment.

Referring to FIG. 2, original images of multiple brain images are transformed into an original radiomic through an image conversion module, and a synthetic image synthesized through the counterfactual reasoning of the original image is converted into synthetic radiomic.

Here, the brain image may be a magnetic resonance image of a brain.

In addition, radiomic is quantitative and high-dimensional data obtained by converting brain images. The radiomic according to the present embodiment may be a gray matter density map (GM). Hereinafter, as the radiomic according to the present embodiment, the gray matter density map will be described as an example, but the present embodiment is not necessarily limited thereto.

According to the present embodiment, before converting into the original gray matter density map and the synthetic gray matter density map, a normal original image is synthesized into a brain disease synthetic image using the counterfactual map, and the brain disease original image is synthesized into a normal synthetic image.

The normal original image and the brain disease synthetic image thereof and the brain disease original image and the normal synthetic image thereof form a data pair.

In the present embodiment, the counterfactual reasoning is performed to determine a prediction model C for diagnosing a clinical stage of Alzheimer's spectrum (i.e., cognitively normal (CN)/mild cognitive impairment (MCI)/Alzheimer's disease (AD)).

According to the present embodiment, it is configured to include several main components such as a counterfactual map generator (CMG), a reasoning evaluator (RE), and a discriminator (DC).

The counterfactual map generator creates a counterfactual map for an arbitrary target label, and the reasoning evaluator effectively guides the counterfactual map generator to understand target label properties when synthesizing the actual desired image. In addition, by utilizing the discriminator to carefully evaluate the original and synthetic images (i.e., r-sMRI and c-sMRI), the counterfactual map generator realistically converts the synthetic image. The reasoning evaluator is defined as the pre-trained prediction model C, and the structure of the discriminator is mimicked identically in the prediction model C.

Initially, the pre-training of the prediction model C is performed using a training sample X and a one-hot encoded correct answer label y.

$$\mathcal{L}_{\text{cls}}^{\mathcal{C}} = \mathbb{E}_{X \sim P_X}[\text{CE}(\mathcal{C}(X), y)], \qquad \text{[Equation 1]}$$

Here, CE is a cross-entropy function.

Hereinafter, in the subsequent training step for generating the visual description of the counterfactual, weights of the reasoning evaluator are modified and at the same time trainable parameters of the discriminator D are adjusted along with the counterfactual map generator G.

The counterfactual map generator is a variant of conditional GAN (CGAN) designed to effectively synthesize a counterfactual map conditional on a target label t. Here, $t \in [0,1]^{|y|}$, and $|y|$ is the size of class space Y.

Given the original image X, the synthetic image c-sMRI $\tilde{X}$ may be inferred as $\tilde{X} = X + M_{X,t}$ according to a specific target counterfactual map $M_{X,t}$.

The counterfactual map generator should be optimized to generate such a counterfactual map so that the synthetic image is diagnosed with the target label t with high confidence.

In particular, the architecture of the counterfactual map generator is configured to include an encoder $\varepsilon_\theta$ and a generator $\mathcal{G}_\varphi$, i.e., a variant of U-Net with the target label t coupled to a skip connection. A subscript $\theta$ of the encoder $\varepsilon_\theta$ and the generator $\mathcal{G}_\varphi$ denotes learnable parameters of each network.

$\varepsilon_\theta$ is copied from the pre-trained prediction model $\mathcal{C}$ in both the architecture and weights (fixed). Therefore, the encoder $\varepsilon_\theta$ is suitable for extracting meaningful representation reflecting class-related discrimination features from the original image.

Since the CMG needs to consider the target label t to generate the counterfactual map, the target-specific features are fused to the feature map obtained from the encoder $\varepsilon_\theta(X)$ through concatenation.

To this end, the target labels are tiled to match the shapes corresponding to each feature map of an 1-th convolutional layer. The size of the tiled target label is $w_l \times h_l \times d_l \times c_l$, each of which is the width, height, depth, and number of channels of the feature map in the l-th convolution block.

To obtain a hierarchical discrimination representation for the target label, an additional module composed of a trainable 3×3×3 kernel and a convolution operation (Conv3D) with a stride of 1 and zero padding in each dimension is provided, and a non-linear leaky-ReLU activation function (LReLU) is as follows.

$$\tau\left(F_l^{\varepsilon_\theta(X)}, t\right) = LReLU\left(Conv3D\left(F_l^{\varepsilon_\theta(X)} \oplus \text{Tile}(t)\right)\right), \qquad \text{[Equation 2]}$$

Here, $\oplus$ denotes a channel-wise concatenation operator, and $$\left\{F_l^{\varepsilon_\theta(X)}\right\}_{l=1}^L$$

denotes an output feature map of an L convolution layer in the encoder $\varepsilon_\theta(X)$. Thereafter, the target fusion feature map $$\tau\left(F_l^{\varepsilon_\theta(X)}, t\right)$$

is transmitted to a generator G via the skip connection. Next, the generator G may smoothly generate the counterfactual map from the target label feature map.

$$M_{X,t} = \mathcal{G}_{\phi}(\mathcal{T}(X,t)), \qquad \text{[Equation 3]}$$

Here, $\mathcal{T}(X,t) = \{\mathcal{T}(F_1^{\varepsilon_\theta(X)}, t), \ldots, \mathcal{T}(F_L^{\varepsilon_\theta(X)}, t)\}$.

Finally, the synthetic image is generated by integrating the input original image and the counterfactual map using addition. That is, the synthetic image should be diagnosed with the target label t.

According to the present embodiment, adversarial training is used to generate the synthetic image.

In particular, a least square GAN (LSGAN) loss function that forces stable optimization by penalizing a sample that is far from a decision boundary of the discriminator is employed. Depending on this loss, the discriminator assists the CMG to minimize significant distances between the actual and generated distributions. Therefore, the discriminator's loss $\mathcal{D}_\psi$ and the generator's loss $\mathcal{G}_\phi$ are respectively defined as follows.

$$\mathcal{L}_{adv}^{D_\psi} = \mathbb{E}_{\tilde{X} \sim P_X}\left[(\mathcal{D}_\psi(\tilde{X}) - 1)^2\right] + \frac{1}{2}\left(\mathbb{E}_{X \sim P_X}\left[\mathcal{D}_\psi(\tilde{X})^2 + \mathcal{D}_\psi(X')^2\right]\right) \qquad \text{[Equation 4]}$$

$$\mathcal{L}_{adv}^{G_\phi} = \frac{1}{2}\left(\mathbb{E}_{X \sim P_X}\left[(\mathcal{D}_\psi(\tilde{X}) - 1)^2 + (\mathcal{D}_\psi(X') - 1)^2\right]\right) \qquad \text{[Equation 5]}$$

Here, $X' = \tilde{X} + M_{\tilde{X},t}$ denotes an override synthetic image of $\tilde{X}$.

$M_{\tilde{X},t}$ denotes a counterfactual map re-defining $\tilde{X}$ to obtain $X'$ expected to be similar to the original image X limited by the posterior probability $t' = \mathcal{C}(X)$.

Because the discriminator is only used to differentiate between the input original image and the synthetic image, it has no immediate ability to explicitly guide the CMG to preserve the shape of the input or to accept target attributes during generation. Therefore, an improved target-dependent counterfactual map is generated using auxiliary cycle consistency loss based on l.

$$\mathcal{L}_{cyc} = \mathbb{E}_{X \sim P_X, t \sim U(0,|y|)}\|X' - X\|_1 \qquad \text{[Equation 6]}$$

Here, $P_X$ denotes a distribution of MRI samples and $t \sim U(0,|y|)$ denotes a one-hot encoded vector randomly drawn from a discrete uniform distribution.

According to the present embodiment, a total variation loss is additionally used to adjust the sophisticated synthesis between the input original image and the counterfactual map. In particular, the total variation loss ensures that the visual consistency of the actual original image is maintained by applying local spatial continuity and smoothness to alleviate unnaturalness of the synthetic image. The normalization for this is shown as follows.

$$\mathcal{L}_{tv} = \qquad \text{[Equation 7]}$$
$$\sum_{i,j,k}\left|\tilde{X}_{i+1,j,k} - \tilde{X}_{i,j,k}\right| + \left|\tilde{X}_{i,j+1,k} - \tilde{X}_{i,j,k}\right| + \left|\tilde{X}_{i,j,k+1} - \tilde{X}_{i,j,k}\right|$$

Here, $\tilde{X} = X + M_{X,t}$ and i, j, and k denote 3D coordinates of each index in a volume image. In addition, elastic normalization is applied to the CMG to impose constraints on the size of the counterfactual map. By doing so, the most granular features are highlighted for the counterfactual reasoning such that minimal modifications to the features lead to predictions that transform the posterior probability $t' = \mathcal{C}(X)$ to the target label t.

$$\mathcal{L}_{map} = \mathbb{E}_{X \sim P_X}[\lambda_1 \|M_{X,t}\|_1 + \lambda_2 \|M_{X,t}\|_2] \qquad \text{[Equation 8]}$$

Here, $\lambda$ and $\lambda$ denote weight constants as hyperparameters.

By additionally using the classification loss feature with proper support for the generator to transform the input original image, the counterfactual map that is accurately classified with the target label t is generated.

$$\mathcal{L}_{cls} = \mathbb{E}_{X \sim P_X}[CE(\tilde{y}, t)] \qquad \text{[Equation 9]}$$

Here, $\tilde{y} = \mathcal{C}(\tilde{X})$ is the softmax activation probability for the synthetic image $\tilde{X}$.

As a result, it defines a composite objective function for the entire counterfactual map generation task as follows.

$$\mathcal{L}_{CMG} = \lambda_3 \mathcal{L}_{adv}^{G_\phi} + \lambda_4 \mathcal{L}_{adv}^{D_\psi} + \lambda_5 \mathcal{L}_{cyc} + \lambda_6 \mathcal{L}_{cls} + \lambda_7 \mathcal{L}_{tv} + \mathcal{L}_{map} \qquad \text{[Equation 10]}$$

Here, a $\lambda$ value is a hyperparameter of the model (including $\lambda_{1,2}$ of Equation 8). $\lambda$ is empirically adjusted so that a magnitude of gradients for each loss term is approximately balanced.

According to the present embodiment, for the task of quantifying the explainability of the counterfactual-based deep features acquired in terms of Alzheimer's disease (AD) diagnosis, i) gray matter density map (GM) acquisition, ii) AD-related representative region of interest extraction, and finally, iii) counterfactual-guided attentive feature representation module learning are performed.

The gray matter density map is acquired through image manipulation, and accurate numerical measurement and quantitative feature-based analysis of brain disease may be performed using the gray matter density map.

To this end, the gray matter density map including counterfactual-guided deep features by reversing the pre-processing procedure used to obtain the training preparation input (i.e., the original image, r-sMRIs) X is acquired from the raw brain image B.

In order to convert the original image and the synthetic image generated as described above into the original gray matter density map and the synthetic gray matter density map, the image conversion module performs preprocessing, brain region segmentation, and denoising.

Figure 3:
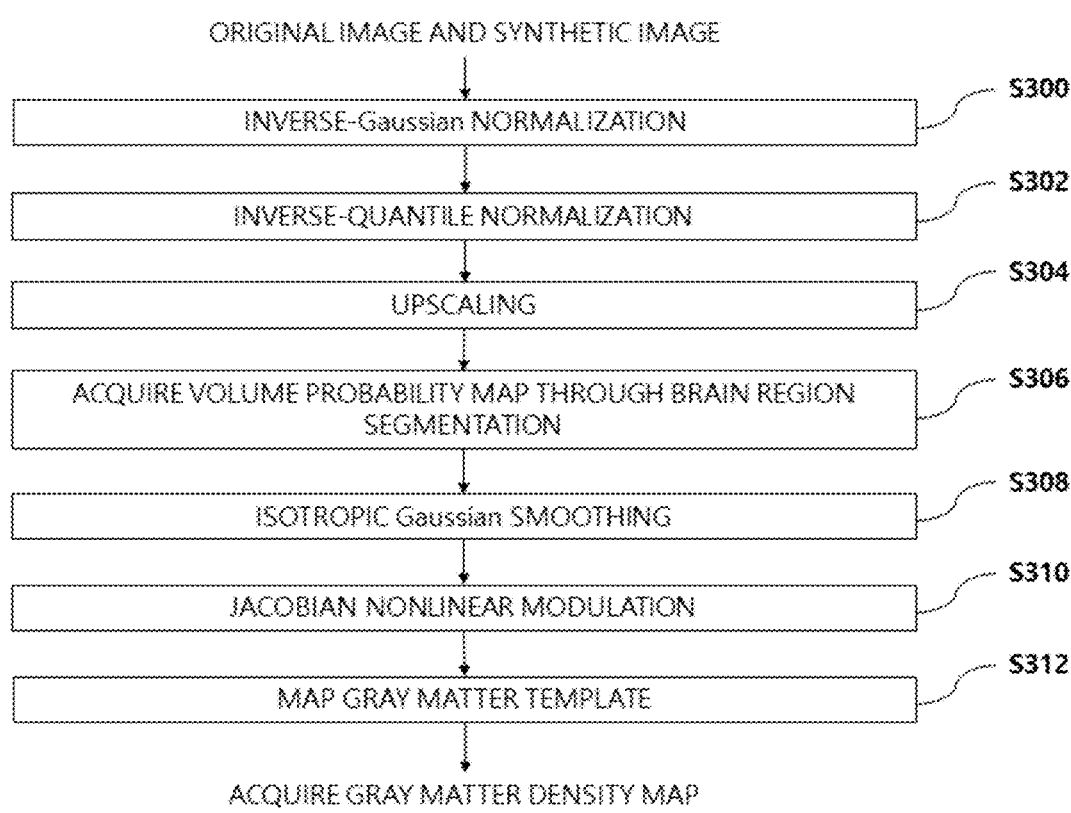
FIG. 3 is a diagram illustrating a process of processing an image conversion module according to the present embodiment.

FIG. 3 is a diagram illustrating a process of processing an image conversion module according to the present embodiment.

As illustrated in FIG. 3, the image conversion module according to the present embodiment largely performs a reverse processing process for inverse transformation to a state before being used as an input of a deep learning model and a preprocessing process for converting a gray matter density map to acquire the gray matter density map.

In order to inversely transform the original image and the synthetic image into the image scale of the state before being used as input to the deep learning model, the image conversion module performs inverse-Gaussian normalization (step 300), inverse-quantile normalization (step 302), upscaling (step 304).

Next, a volume probability map is acquired by performing the brain region segmentation on three regions of brain region, gray matter, white matter, and cerebrospinal fluid (step 306).

Then, in order to perform structural distortion, the volume probability map is mapped to a gray matter template (step

308) and converted into the gray matter density map through Jacobian non-linear modulation (step 310).

Finally, the original gray matter density map and the synthetic gray matter density map are derived by alleviating unrelated noise or contrast generated in the preprocessing process through isotropic Gaussian smoothing (step 312).

More specifically, instead of considering a raw brain image B in inverse quantile normalization, an input of model X is employed as an alternative ground-truth. Similar inverse pre-processing is performed on the synthetic image. Then, a final inverted raw image B' is acquired through upscaling to match a size (i.e., 193×229×193) of the raw brain image B.

Finally, an auxiliary step is performed to obtain the gray matter density map for the B' set, which is as follows.

(i) An image extracted from a brain is segmented into gray matter (GM), white matter (WM), and cerebrospinal fluid (CSF) volume probability maps using FMRIB's automated segmentation tool (FAST).

(ii) A gray matter template is generated by registration in MNI 152 space using FMRIB's linear affine registration tool (FLIRT). After non-linear registration using FMRIB's non-linear registration tool (FNIRT), an average of the result images is obtained to generate the gray matter template.

(iii) Also, all gray matter images are non-linearly registered to the template and modulated using Jacobian of a warp field. (iv) The images are smoothed with an isotropic Gaussian kernel with σ of 2 mm to alleviate contrast and other unrelated details in the image.

When the gray matter density map is acquired, the validity of counterfactual-guided deep features is additionally investigated by utilizing gray matter density-based analysis.

According to the present embodiment, a representative region of interest for brain disease prediction is extracted by estimating a difference between the original gray matter density map and the synthetic gray matter density map acquired as described above.

Figure 4:
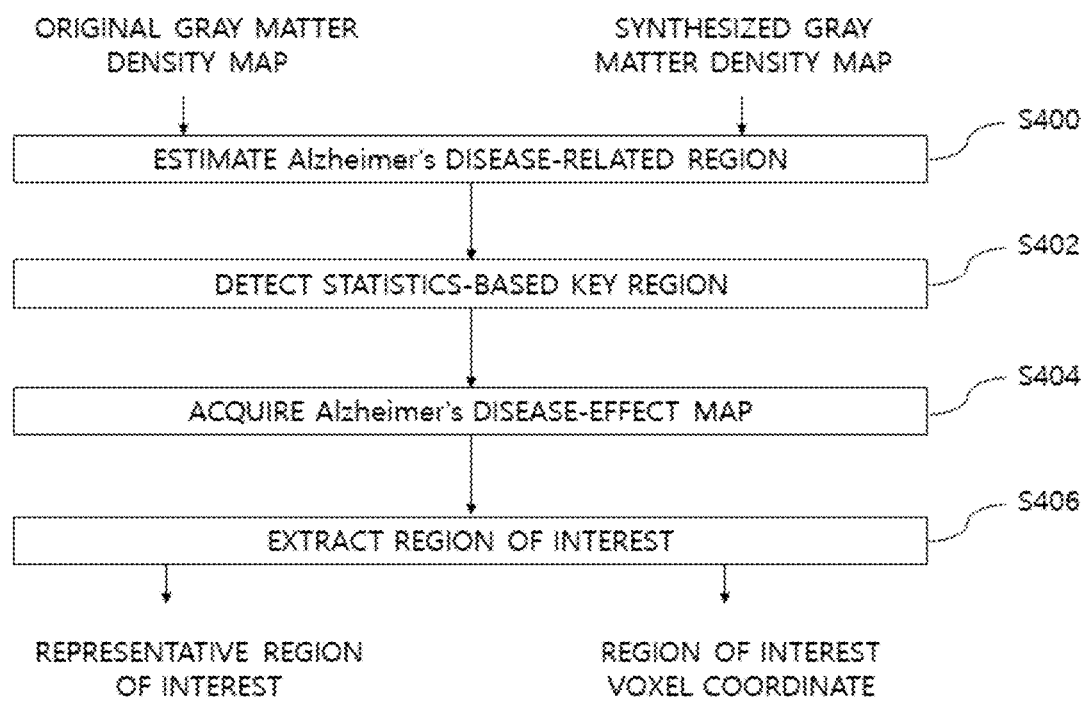
FIG. 4 is a diagram illustrating a process of extracting a representative region of interest according to the present embodiment.

FIG. 4 is a diagram illustrating a process of extracting a representative region of interest according to the present embodiment.

Referring to FIG. 4, the Alzheimer's disease-related region is estimated by calculating the difference between the original gray matter density map and the synthetic gray matter density map (step 400), and the average of the absolute values of the difference between all the calculated gray matter density maps is calculated to detect a statistics-based key region (step 402).

Through the above process, an Alzheimer's disease-effect map reflecting differences in structural changes in the brain is acquired (step 404).

In step 404, the brain disease-effect map including a brain disease representative region is acquired by applying a constraint to a brain disease, that is, Alzheimer's disease-related region through a statistical percentile threshold.

Next, the representative regions of interest are extracted from values corresponding to prominent regions in the Alzheimer's disease-affect map through the brain region segmentation, and voxel coordinates corresponding thereto are also acquired (step 406).

Figure 5:
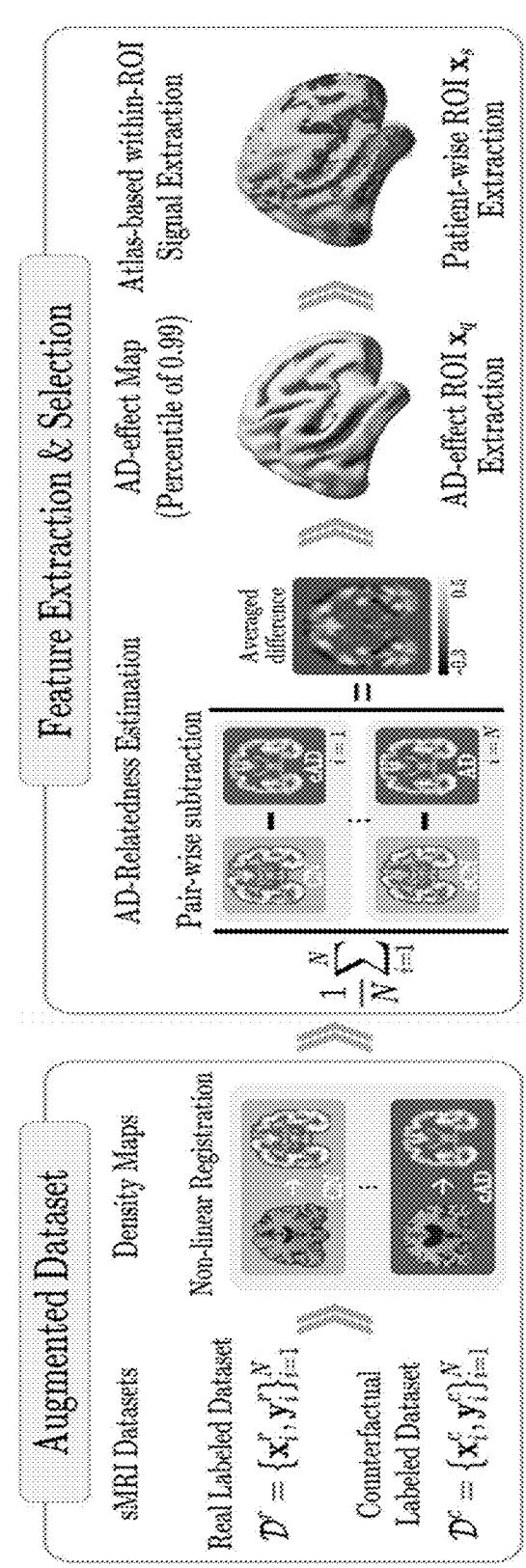
FIG. 5 is a diagram illustrating original radiomic and synthetic radiomic transformations and the process of extracting a representative region of interest according to the present embodiment.

FIG. 5 is a diagram illustrating a process of converting into an original gray matter density map and a synthesized gray matter density map and extracting a representative region of interest according to the present embodiment.

In FIG. 5, Dr denotes an original image, Dc denotes a synthetic image, blue denotes normal, and red denotes a gray matter density map of Alzheimer's disease.

An Alzheimer's disease-effect map $x_q$ is acquired using the average of the differences between the original gray matter density maps and the synthetic gray matter density maps, and the representative region of interest is extracted using the $x_q$.

According to the present embodiment, after the representative region of interest is extracted, the representative region of interest and brain images for each patient are applied to a linear classifier including a counterfactual-guided attentive feature representation module to predict a disease state.

Figure 6:
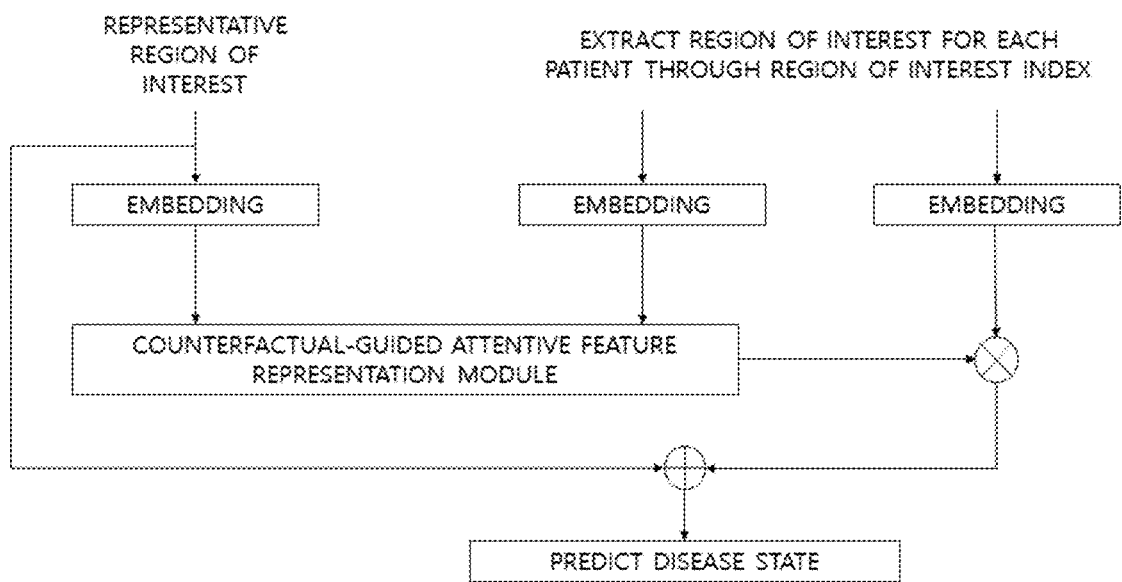
FIG. 6 is a diagram illustrating a detailed configuration of a linear classifier including a counterfactual-guided attentive feature representation module according to the present embodiment.

FIG. 6 is a diagram illustrating a detailed configuration of a linear classifier including a counterfactual-guided attentive feature representation module according to the present embodiment.

Referring to FIG. 6, a region of interest is extracted from brain images for each patient based on its voxel coordinates acquired together with the representative region of interest to acquire a counterfactual-guided attention map, and the disease state of the corresponding patient is predicted using the acquired counterfactual-guided attention map.

More specifically, the linear classifier according to the present embodiment embeds the representative region of interest and the brain images for each patient, respectively, and converts the representative region of interest and the brain images into an embedding matrix, multiply the embedding matrix corresponding to the representative region of interest and the embedding matrix of the brain images for each patient element by element to generate a counterfactual-guided attention map, and predicts the disease state using the counterfactual-based attention map and a calculation result of the embedding matrix of the brain images for each patient.

To define the three inputs for learning the counterfactual-based feature representation, the representative region of interest and the voxel coordinates corresponding thereto are used.

Figure 7:
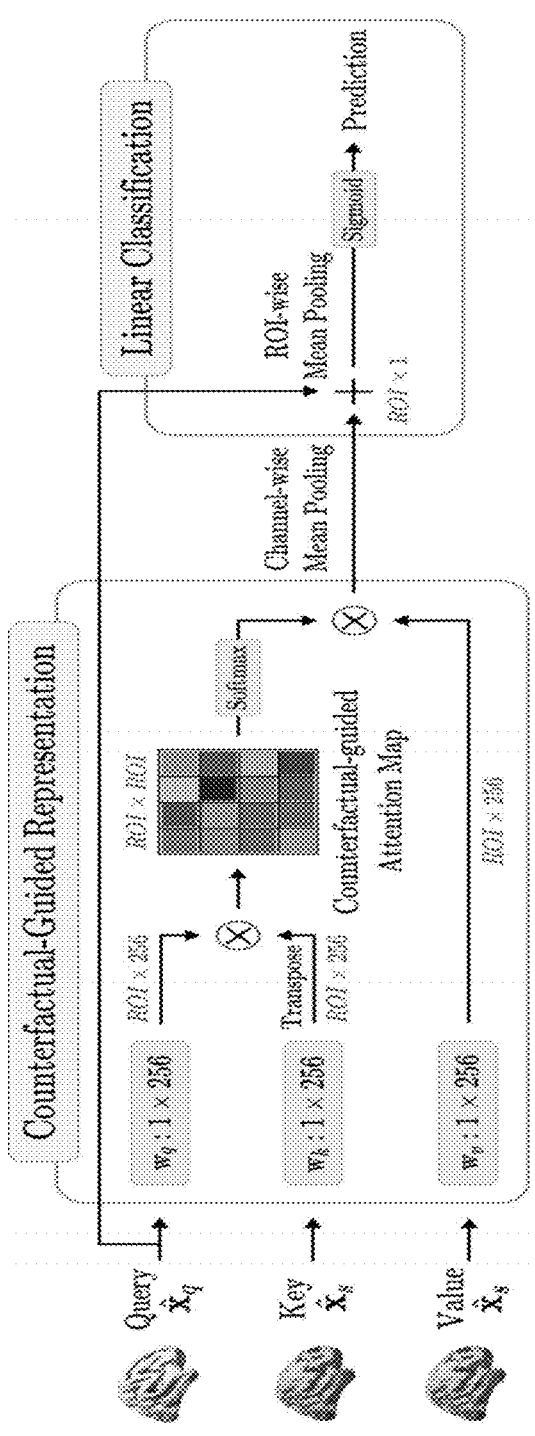
FIG. 7 is a diagram illustrating a disease prediction system including a counterfactual-guided attentive feature representation module according to the present embodiment.

FIG. 7 is a diagram illustrating a disease prediction system including a counterfactual-guided attentive feature representation module according to the present embodiment.

First, the representative region of interest (Query, $x_q$) is used as a fixed input in the learning process, while the remaining two inputs (key $x_s$, value $x_s$) extract values matching the corresponding coordinates through the voxel coordinates of the region of interest for each patient to define the region of interest.

For the learning of the feature representation, embedding is performed on each region of interest, the regions of interest are converted into an embedding matrix, and then a counterfactual-guided attentive feature representation module calculation is performed through matrix multiplication.

Based on the calculated counterfactual-guided attentive feature representation module, by multiplying the regions of interest for each patient, an attention map highlighting the regions of interest that are important in the process of predicting the disease states for each patient is generated. Finally, the disease states for each patient are predicted through a linear combination with the representative region of interest.

$\hat{X}^r$ and $\hat{X}^c$ denote the original gray matter and the synthetic gray matter obtained from the original image and the synthetic image, respectively.

First, the original gray matter $\hat{X}^r$ is subtracted from the corresponding synthetic gray matter $\hat{X}^c$ of different clinical stages to obtain a stepwise difference map. For example, for the original gray matter labeled normally, a counterpart of a clinical marker for the synthetic gray matter should be defined as brain disease (AD or MCI) under a given scenario. The advantageous properties of the difference map have discriminative ability to reflect the unique anatomical characteristics of disease-related localization and inter-individual variability.

Next, these difference maps are averaged into an AD effect map $M_{eff}$, using the average of the difference maps as follows.

$$M_{eff} = \frac{1}{N}\sum_{i=1}^{N}|\hat{x}_i^y - \hat{x}_i^c| \qquad \text{[Equation 11]}$$

Here, N and |•| indicate the total number of samples and absolute value calculation respectively. The AD effect map is finally masked by a percentile threshold that clearly represents the most frequently highlighted regions among a set of subdivided regions.

Brain parcellation not only provides an understanding of basic brain organization and function in closely interacting regions, but also compresses information of hundreds of thousands of voxels or vertices into manageable sets.

In the present embodiment, a region of interest-based analysis is employed to extract and analyze a region of interest (ROI) from a voxel-level value representing the AD effect map.

To this end, an automated anatomical labeling (AAL3) atlas is overlaid on the AD effect map and further subdivided into individual regions, and thus, each trimmed region is entirely within cortical and subcortical regions and has anatomical specificity.

As a result, the partitioned region and the corresponding voxel index V are identified using the voxel highlighted in the AD effect map according to the present embodiment. A representative region of interest set composed of R regions of interest, the so-called AD-effect region of interest, is defined as $x_q \in \mathbb{R}^{R \times 1}$ by averaging the voxel values of the index V within the adopted parcellation region.

An objective classification task is performed to further confirm the effect of the acquired AD-effect ROI $x_q$ along with each voxel index V.

According to the present embodiment, a method of effectively highlighting the most important ROI by itself considering a global relationship between ROIs is proposed.

The prediction module according to the present embodiment maps a region of interest set (i.e., vector type) composed of a query, a key, and a value to an input.

According to the present embodiment, the AD-effect region of interest (representative region of interest) is set as a query, and the query is fixed.

Unlike the fixed query in the training stage, the corresponding region of interest is independently extracted from each training sample according to the voxel index V whose key and value are $x_s \in \mathbb{R}^{R \times 1}$ Then, the queries, keys, and values are converted into a set of embedded matrices Q, K, and $V \in \mathbb{R}^{R \times D}$ using an embedding layer $w \in \mathbb{R}^{1 \times D}$. Then, the counterfactual-guided attention matrix of the output is computed as follows.

$$\text{Attention}(Q, K, V) = g\left(\frac{QK^\top}{\sqrt{d}}\right)V \qquad \text{[Equation 12]}$$

Here, T and d denote the number of regions of interest used in the key for transposition and scaling, respectively, and g denotes a softmax function.

The sets Q, K, and V denote embedded matrices generated from linear transformations, $Q = x_q w_q$, $K = x_s w_k$, and $V = x_s w_v$, respectively, wherein, $w_q$, $w_k$, and $w_v$ denote learnable weights.

By applying average pooling for each channel, the output of the counterfactual-guided attentive feature representation module is reconstructed to match the size of the input query, and then residual linkage using element-wise addition is used, and the average pooling for each region of interest is used. The final predicted label $\bar{y}$ is obtained as follows.

$$\bar{y} = \sigma\left(MP_\downarrow\left(MP_\rightarrow\left(g\left(\frac{QK^\top}{\sqrt{d}}\right)V\right) + x_q\right)\right) \qquad \text{[Equation 13]}$$

wherein, $MP_\downarrow$ and $MP_\rightarrow$ denote the average pooling for each region of interest and the average pooling for each channel, respectively, and $\sigma$ denotes a logistic sigmoid function.

Eventually, the linear classifier is trained by minimizing the classification loss through CE as follows.

$$\mathcal{L}_{cls}^{LiCoL} = \mathbb{E}_{\hat{X} \sim P_{\hat{X}}}[CE(\bar{y}, y))] \qquad \text{[Equation 14]}$$

wherein, $\hat{X}$ and y denote the gray matter density maps and the ground-truth label, respectively, and $\bar{y}$ denote the one-hot embedded prediction label.

According to the present invention, it is possible to provide precise numerical interpretation and explanation in terms of a clinical aspect, and by utilizing the precise numerical interpretation and explanation together with the proposed counterfactual-guided attentive feature representation constructed to a linear classifier, it is possible to show intuitive interpretability for improved disease predictive performance based on the transparency of the model.

More specifically, by performing the image conversion from the original image (input) and the synthetic image into the gray matter density map, respectively, performing the segmentation for each brain region from the obtained gray matter density map, and extracting the representative region of interest (ROI) for regions in which the structural changes in the brain are prominent due to the Alzheimer's disease between two images, the quantitative feature analysis is performed. Furthermore, by proposing the linear classifier that considers the relationship between the regions of interest through a counterfactual-guided attentive feature representation calculation, it is possible to derive an Alzheimer's disease-related ADness index in terms of the clinical aspect without additional learning or modules for interpretation and derive excellent predictive performance comparable to the deep learning model although it is the linear model.

The embodiments of the present invention described above have been disclosed for illustrative purposes, and those skilled in the art with ordinary knowledge of the present invention will be able to make various modifications, changes, and additions within the spirit and scope of the present invention, and these modifications, changes, and additions should be regarded as falling within the scope of the following claims.

What is claimed is:

1. A brain image-based quantitative brain disease prediction apparatus, comprising:

a processor; and a memory connected to the processor, wherein the memory stores program instructions executed by the processor to:

convert original images of multiple brain images into original radiomic, convert a synthetic image synthesized through counterfactual reasoning of the original image into a synthetic radiomic, estimate a difference between the original radiomic and the synthetic radiomic to extract a representative region of interest for brain disease prediction, and input the representative region of interest and brain images for each patient to a linear classifier including a counterfactual-guided attentive feature representation module to predict a disease state.

2. The brain image-based quantitative brain disease prediction apparatus of claim 1, wherein the program instructions synthesize a normal original image into a brain disease synthetic image and synthesize a brain disease original image into a normal synthetic image using a counterfactual map, before converting into the original radiomic and the synthetic radiomic.

3. The brain image-based quantitative brain disease prediction apparatus of claim 1, wherein the program instructions perform preprocessing, brain region segmentation, and denoising to convert the original image and the synthetic image into the original radiomic and the synthetic radiomic.

4. The brain image-based quantitative brain disease prediction apparatus of claim 3, wherein the preprocessing comprises inverse-Gaussian normalization, inverse-quantile normalization, and upscaling for inverse transformation to an image scale of a state before being used as an input of a deep learning model.

5. The brain image-based quantitative brain disease prediction apparatus of claim 3, wherein a brain region classified by the brain region segmentation comprises gray matter, white matter, and cerebrospinal fluid, and a volume probability map is obtained by the brain region segmentation.

6. The brain image-based quantitative brain disease prediction apparatus of claim 5, wherein the program instructions map the volume probability map to a gray matter template to perform structural distortion, apply Jacobian non-linear modulation to a result image from the mapping, and remove noise through isotropic Gaussian smoothing and alleviate a contrast generated in the preprocessing.

7. The brain image-based quantitative brain disease prediction apparatus of claim 1, wherein the program instructions calculate the difference between the original radiomic and the synthetic radiomic, estimate a brain disease-related region through an average of absolute values of differences between all the original radiomics and synthetic radiomics, apply a constraint through a statistical percentile threshold to the brain disease-related region to acquire a brain disease-effect map including a brain disease representative region, extract a representative region of interest from a value corresponding to the brain disease representative region in the brain disease-effect map through brain region segmentation, and acquire voxel coordinates corresponding to the representative region of interest.

8. The brain image-based quantitative brain disease prediction apparatus of claim 1, wherein the program instructions embed the representative region of interest and the brain images for each patient, respectively, and convert the representative region of interest and the brain images into an embedding matrix, multiply the embedding matrix corresponding to the representative region of interest and the embedding matrix of the brain images for each patient element by element to generate a counterfactual-guided attention map, and predict the disease state using the counterfactual-based attention map and a calculation result of the embedding matrix of the brain images for each patient.

9. The brain image-based quantitative brain disease prediction apparatus of claim 8, wherein the program instructions multiply the counterfactual-based attention map and the embedding matrix of the brain images for each patient element by element, and predict the disease state using a result of the multiplication and a result of summing the embedding matrix corresponding to the representative region of interest element by element.

10. A brain image-based quantitative brain disease prediction method, comprising:

converting original images of multiple brain images into original radiomic;

converting a synthetic image synthesized through counterfactual reasoning of the original image into a synthetic radiomic;

estimating a difference between the original radiomic and the synthetic radiomic to extract a representative region of interest for brain disease prediction; and inputting the representative region of interest and brain images for each patient to a linear classifier including a counterfactual-guided attentive feature representation module to predict a disease state.

\* \* \* \* \*